United States Patent [19]

Zwingmann

[11] 4,382,909
[45] May 10, 1983

[54] GOLD FREE ALLOYS FOR FIRING ON CERAMIC COMPOSITIONS

[75] Inventor: Gerhard Zwingmann, Bruchkobel, Fed. Rep. of Germany

[73] Assignee: Degussa Aktiengesellschaft, Frankfurt, Fed. Rep. of Germany

[21] Appl. No.: 241,042

[22] Filed: Mar. 6, 1981

[30] Foreign Application Priority Data

Mar. 13, 1980 [DE] Fed. Rep. of Germany ....... 3009650

[51] Int. Cl.³ ...................... C22C 30/00; C22C 19/07; C22C 5/04
[52] U.S. Cl. .................................. 420/588; 420/580; 420/463; 420/436; 420/437
[58] Field of Search ................. 75/172 E, 172 R, 171, 75/134 N, 134 B, 134 F, 176; 433/207

[56] References Cited

U.S. PATENT DOCUMENTS

| | | | |
|---|---|---|---|
| 2,182,041 | 12/1939 | Szabo | 75/171 |
| 2,226,079 | 12/1940 | Spanner | 75/170 X |
| 3,121,629 | 2/1964 | Mann | 75/171 |
| 3,896,547 | 7/1975 | Kulwiec | 433/207 |
| 3,928,913 | 12/1975 | Schaffer | 433/207 |
| 3,976,436 | 8/1976 | Chang | 75/171 X |
| 4,018,569 | 4/1977 | Chang | 75/170 X |
| 4,061,495 | 12/1977 | Selman et al. | 75/134 F |
| 4,149,881 | 4/1979 | D'Silva | 75/134 F |
| 4,239,533 | 12/1980 | Miyazaki | 75/171 X |
| 4,261,742 | 4/1981 | Coupland et al. | 75/134 F |

FOREIGN PATENT DOCUMENTS 68795 6/1915 Austria .
684186 12/1939 Fed. Rep. of Germany .

*Primary Examiner*—L. Dewayne Rutledge
*Assistant Examiner*—David Hey
*Attorney, Agent, or Firm*—Cushman, Darby & Cushman

[57] ABSTRACT

There is provided a gold free alloy for firing on ceramic compositions, especially for dental purposes consisting essentially of 1–70 weight % palladium, 0.1–35 weight % chromium, and the balance consisting essentially of cobalt. There can also be present up to 1 weight % boron, up to 20 weight % molybdenum and/or tungsten, up to 8 weight % scandium, yttrium, lanthanum and/or the rare earths and up to 5 weight % aluminum, silicon, tin, indium and/or gallium.

22 Claims, No Drawings

GOLD FREE ALLOYS FOR FIRING ON CERAMIC COMPOSITIONS

BACKGROUND OF THE INVENTION

The invention is directed to a gold free alloy for the firing on of ceramic compositions, especially for industrial dental purposes.

For many years gold containing noble metal alloys having high contents of gold have been used for artificial teeth overcoated with dental procelain. These known alloys are very well suited for this purpose and lead to good adhering, normally crack free procelain overlays. Because of their relatively low melting temperatures they are readily workable and because of their high portion of noble metal they are very resistant to corrosion.

Because of the high price of gold and the high density of these known alloys there have been previously many attempts to replace these high gold containing alloys through those based on silver-palladium or on a non-noble metal basis. Such non-noble metal alloys previously always contained nickel as the chief component, besides, in many cases, beryllium also as a component of the alloy. Both elements however, are toxic and therefore little suited for use in the human mouth.

Besides these nickel alloys generally show a high solidus temperature which makes their use in dental laboratories very difficult. Besides, compared to high gold content alloys, they have a reduced resistance to corrosion which, to be sure can be improved by a high chromium content. However, the addition of chromium leads to green coloration of the porcelain in the firing on of porcelain, which coloration is undesired.

The same disadvantage is also shown by the known fired on alloys based on silver-palladium.

Recently, there have become known non-noble metal alloys based on cobalt for the firing on of dental porcelains which contain either no noble metals or insignificant amounts thereof. Since cobalt, however, in contrast to nickel is only resistant to corrosion with chromium contents of more than 25 weight %, this makes the green coloration of the porcelain in the firing noticeable. Besides in these alloys the adhesive strength of the fired porcelain is not sufficient.

Therefore it was the problem of the present invention to find gold free alloys for the firing on of ceramic compositions, especially for industrial dental purposes which contain no toxic components, are corrosion resistant, have a relatively low melting point, do not cause coloration of the ceramic compositions in the firing and guarantee an adhesive bond.

SUMMARY OF THE INVENTION

This problem was solved according to the invention by using alloys which consists of (or consist essentially of) 1-70 weight % palladium, 0.1-35 weight % chromium, balance consists of (or consisting essentially of) cobalt. Preferably these alloys contain 5-40 weight % palladium and 3-25 weight % chromium.

It has surprisingly been found that palladium additions to cobalt or cobalt with a relatively low chromium contents very greatly increase the corrosion resistance and the adhesive strength of these alloys for ceramic compositions. For example an alloy of 45% cobalt with 54.8% palladium and 0.2% chromium corresponds in its breakdown potential (0.1 normal NaCl solution) already to that of pure palladium. At low palladium contents there can be attained a high corrosion resistance by the addition of comparatively slight amounts of chromium (up to 35 weight %). Ternary cobalt chromium-palladium alloys are very well suited for alloys to be fired in the dental range.

For establishing a low melting temperature necessary for an easy workability and for a better casting behavior there are advantageously added to the alloys of the invention boron in an amount up to 1 weight %, e.g. 0.02 to 1 weight %. Thereby the melting temperature of the alloys having a high palladium content are greatly lowered by the addition of boron so that with increasing palladium content in the alloys the addition of boron can be reduced.

For improved control of the hardness, the tensile strength, the elongation at break and to a certain extent the thermal coefficient of expansion there advantageously is added to the alloys of the invention up to 20 weight % molybdenum, and/or tungsten, e.g. 0.5 to 20 weight % of molybdenum.

A good adhesive strength of the ceramic compositions to the metallic fired alloys can only be attained if the thermal coefficient expansion of the ceramic composition and alloy are about the same. Besides there is needed the formation of a certain adhesive oxide layer on the alloy in the firing of the ceramic composition. Alloys having high cobalt contents and relatively low chromium portions at higher temperatures such as are necessary for the firing of dental porcelain tend to form relatively thick scale layers which in certain cases can damage the adhesive strength of the porcelain layers.

Therefore it has proven good to add to the alloys of the invention up to 8 weight % of scandium, yttrium, lanthanum, cerium and/or other rare earths, e.g. 0.5 to 8 weight % which greatly retards the formation of a scale layer. Besides through these additives there is partially reduced the tendency present to form cracks in the fired on ceramic compositions.

At higher palladium contents an additive of up to 5 weight % of aluminum, silicon, tin, indium and/or gallium, e.g. 0.1 to 5 weight % has proven advantageous.

Especially advantagous are alloys which consist of cobalt together with 24-35 weight % palladium, 5-15 weight % chromium, 5-15 weight % molybdenum and/or tungsten, 2-6 weight % cerium and 0.2-0.8 weight % boron.

The alloys of the invention can consist essentially of or consist of the stated elements.

Unless otherwise indicated all parts and percentages are by weight.

The alloys of the invention can be faced with all of the commercial ceramic compositions for industrial dental purposes with good adhesive strength and without there occurring the formation of cracks or a coloration. Thus, for example, there were produced 50 teeth crowns in each case of an alloy of the invention having 45.6% Co, 30% Pd, 10% Cr, 10% Mo, 4% Ce, and 0.4% B, of a commercial high gold containing firing alloy, as well as of a commercial non-noble metal-firing alloy based on nickel and these crowns were coated with a commercial porcelain composition at 950° C. None of the crowns made of the alloy of the invention after firing showed cracks in the porcelain while there occurred two cracks with the high gold containing alloy and five cracks with the nickel alloy. Also after long storage time the crown of the alloy of the invention did not show so-called "late cracks".

The table shows the properties of several alloys of the invention in comparison to known high gold containing and nickel containing firing alloys. Thereby the measurement of corrosion was carried out potentiostatically in 0.1 N sodium chloride solution and elongation at break $E_L$ determined. Tensile strength, elongation at break and hardness were measured on rods produced by centrifugal casting with inductive heating.

For determination of the adhesive strength of the porcelain to the base-material sheet metal strips of the alloy were coated on one side with porcelain, thereupon a second sheet metal strip applied with a high-strength adhesive and this bond tested in a tensile testing machine.

The entire disclosure of German priority application Ser. No. P3009650.5 is hereby incorporated by reference.

| | Alloy | Breakdown potential $E_L$ [nV] | Tensile Strength $\sigma_\beta$ [N/mm²] | Elongation at break δ [%] | Hardness | Termal Expansion Coefficient α(10–500° C.) · 10⁻⁶ | Adhesive strength [N/mm²] | Fired on Properties |
|---|---|---|---|---|---|---|---|---|
| 1 | 60Co 10Cr 30Pd | +350 | 710 | 10 | 290 | 14,0 | | satisfactory |
| 2 | 71,6Co 20Cr 5Pd 1,2 Si 1,2 Al 1B | +45 | 820 | 5 | 380 | 14,3 | | satisfactory |
| 3 | 67Co 17,5Cr 5Pd 10Mo 0,5B | +20 | 810 | 6 | 360 | 14,8 | | satisfactory |
| 4 | 60Co 15Cr 10Pd 12,5 Mo 2Sn 0,5B | +120 | 790 | 6 | 330 | 14,9 | | good |
| 5 | 45,6Co 10Cr 30Pd 10Mo 4Ce 0,4B | +350 | 880 | 7 | 350 | 15,1 | 5,1 | very good |
| 6 | 26,95Co 5Cr 50Pd 15Mo 3Y 0,05B | +995 | 810 | 9 | 280 | 14,9 | 4,9 | good |
| 7 | 35Co 1Cr 60Pd 2Sn 2Dn | +1055 | 710 | 12 | 250 | 14,8 | | good |
| 8 | Commercial high gold containing alloy | +450 | 650 | 7 | 240 | 14,5 | 3,1 | good |
| 9 | Commercial nickel containing alloys | +35 | 700 | 5 | 320 | 14,5 | 3,8 | satisfactory |

What is claimed is:

1. A gold free alloy suitable for firing on ceramic compositions for dental purposes consisting essentially of 1–70 weight % palladium, 0.1–35 weight % chromium, 0.2 to 1 weight % boron, and the balance consisting essentially of cobalt.

2. A gold free alloy suitable for firing on ceramic compositions for dental purposes consisting essentially of 1–70 weight % palladium, 0.1–35 weight % chromium, also containing boron, the boron being present in an amount of up to 1 weight % and containing molybdenum, tungsten, or a mixture of molybdenum and tungsten, said molybdenum, tungsten, or mixture thereof being present in an amount of up to 20 weight %, and the balance consisting essentially of cobalt.

3. A gold free alloy according to claim 2 containing an element which is scandium, yttrium, lanthanum, another rare earth or mixture of such elements, said element or mixture of elements being present in an amount of up to 8 weight %.

4. A gold free alloy according to claim 3 containing aluminum, silicon, tin, indium, gallium or mixture thereof, said aluminum, silicon, tin, indium, gallium or mixture thereof being present in an amount of up to 5 weight %.

5. A gold free alloy according to claim 2 containing aluminum, silicon, tin, indium, gallium or mixture thereof, said aluminum, silicon, tin, indium, gallium or mixture thereof being present in an amount of up to 5 weight %.

6. A gold free alloy suitable for firing on ceramic compositions for dental purposes consisting essentially of 5–40 weight % palladium, 3–25 weight % chromium, also containing boron, the boron being present in an amount of up to 1 weight % and containing molybdenum, tungsten, or a mixture of molybdenum and tungsten, said molybdenum, tungsten, or mixture thereof being present in an amount of up to 20 weight %, and the balance consisting essentially of cobalt.

7. A gold free alloy according to claim 6 containing an element which is scandium, yttrium, lanthanum, another rare earth or mixture of such elements, said element or mixture of elements being present in an amount of up to 8 weight %.

8. A gold free alloy according to claim 7 containing aluminum, silicon, tin, indium, gallium or mixture thereof, said aluminum, silicon, tin, indium, gallium or mixture thereof being present in an amount of up to 5 weight %.

9. A gold free alloy according to claim 6 containing aluminum, silicon, tin, indium, gallium or mixture thereof, said aluminum, silicon, tin, indium, gallium or mixture thereof being present in an amount of up to 5 weight %.

10. A gold free alloy suitable for firing on ceramic compositions for dental purposes consisting essentially of 1–70 weight % palladium, 0.1–35 weight % chromium, also containing boron, the boron being present in an amount of up to 1 weight % and containing an element which is scandium, yttrium, lanthanum, another rare earth or mixture of such elements, said element or mixture of elements being present in an amount of up to 8 weight %, and the balance consisting essentially of cobalt.

11. A gold free alloy according to claim 10 containing aluminum, silicon, tin, indium, gallium or mixture thereof, said aluminum, silicon, tin, indium, gallium or mixture thereof being present in an amount of up to 5 weight %.

12. A gold free alloy suitable for firing on ceramic compositions for dental purposes consisting essentially of 5–40 weight % palladium, 3–25 weight % chromium, also containing boron, the boron being present in an amount of up to 1 weight % and containing an element which is scandium, yttrium, lanthanum, another rare earth or mixture of such elements, said element or mixture of elements being present in an amount of up to 8 weight %, and the balance consisting essentially of cobalt.

13. A gold free alloy according to claim 12 containing aluminum, silicon, tin, indium, gallium or mixture thereof, said aluminum, silicon, tin, indium, gallium or mixture thereof being present in an amount of up to 5 weight %.

14. A gold free alloy suitable for firing on ceramic compositions for dental purposes consisting essentially of 1–70 weight % palladium, 0.1–35 weight % chromium, containing aluminum, silicon, tin, indium, gallium, or mixture thereof, said aluminum, silicon, tin, indium, gallium, or mixture thereof being present in an amount of up to 5 weight %, and the balance consisting essentially of cobalt.

15. A gold free alloy suitable for firing on ceramic compositions for dental purposes consisting essentially of 5–40 weight % palladium, 3–25 weight % chromium, containing aluminum, silicon, tin, indium, gallium, or mixture thereof, said aluminum, silicon, tin, indium, gallium, or mixture thereof being present in an amount of up to 5 weight %, and the balance consisting essentially of cobalt.

16. A dental ceramic composition having fired thereon as a facing of gold free alloy selected from the group consisting of (1) 1–70 weight % palladium, 0.1–35 weight % chromium and the balance consisting essentially of cobalt, (2) 1–70 weight % palladium, 0.1–35 weight % chromium, boron, the boron being present in an amount of up to 1 weight % and the balance consisting essentially of cobalt, (3) 1–70 weight % palladium, 0.1–35 weight % chromium, at least one member of the group consisting of molybdenum and tungsten, said member being present in an amount of up to 20 weight % and the balance consisting essentially of cobalt, (4) an alloy as in (3) but also containing boron, the boron being present in an amount of up to 1%, (5) an alloy as in (4) also containing at least one element from the group consisting of scandium, yttrium, lanthanum and another rare earth element, said element being present in an amount of up to 8 weight %, (6) an alloy as in (3) also containing at least one element from the group consisting of scandium, yttrium, lanthanum and another rare earth element, said element being present in an amount of up to 8 weight %, (7) an alloy as in (2) also containing at least one element from the group consisting of scandium, yttrium, lanthanum and another rare earth element, said element being present in an amount of up to 8 weight %, (8) an alloy as in (1) also containing at least one element from the group consisting of scandium, yttrium, lanthanum and another rare earth element, said element being present in an amount of up to 8 weight %, (9) an alloy as in (8) also containing at least one element from the group consisting of aluminum, silicon, tin, indium and gallium, said element being present in an amount of up to 5 weight %, (10) an alloy as in (7) also containing at least one element from the group consisting of aluminum, silicon, tin, indium and gallium, said element being present in an amount of up to 5 weight %, (11) an alloy as in (6) also containing at least one element from the group consisting of aluminum, silicon, tin, indium and gallium, said element being present in an amount of up to 5 weight %, (12) an alloy as in (5) also containing at least one element from the group consisting of aluminum, silicon, tin, indium and gallium, said element being present in an amount of up to 5 weight %, (13) an alloy as in (4) also containing at least one element from the group consisting of aluminum, silicon, tin, indium and gallium, said element being present in an amount of up to 5 weight %, (14) an alloy as in (3) also containing at least one element from the group consisting of aluminum, silicon, tin, indium and gallium, said element being present in an amount of up to 5 weight %, (15) an alloy as in (2) also containing at least one element from the group consisting of aluminum, silicon, tin, indium and gallium, said element being present in an amount of up to 5 weight %, (16) an alloy as in (1) also containing at least one element from the group consisting of aluminum, silicon, tin, indium and gallium, said element being present in an amount of up to 5 weight %, or (17) consisting of 25–35 weight % palladium, 5–15 weight % chromium, 5–15 weight % molybdenum, tungsten or a mixture thereof, 2–6 weight % cerium, 0.2–0.8 weight % boron and the balance cobalt.

17. A crown made of the alloy of claim 16 faced with a dental ceramic composition.

18. A gold free alloy suitable for firing on ceramic compositions for dental purposes consisting essentially of 1–70 weight % palladium, 0.1–35 weight % chromium, also containing molybdenum, tungsten or mixture of molybdenum and tungsten, said molybdenum, tungsten or mixture thereof being present in an amount of up to 20 weight %, containing an element which is scandium, yttrium, lanthanum, another rare earth or mixture of such elements, said element or mixture of elements being present in an amount of up to 8 weight % and the balance consisting essentially of cobalt.

19. A gold free alloy according to claim 18 containg 5–20 weight molybdenum, tungsten or a mixture thereof.

20. A gold free alloy according to claim 18 containing aluminum, silicon, tin, indium, gallium or mixture thereof, said aluminum, silicon, tin, indium, gallium or mixture thereof being present in an amount of up to 5 weight %.

21. A gold free alloy suitable for firing on ceramic compositions for dental purposes consisting of 25–35 weight % palladium, 5–15 weight % chromium, 5–15 weight % molybdenum, tungsten or a mixture thereof, 2–6 weight % cerium, 0.2–0.8 weight % boron and the balance cobalt.

22. A gold free alloy suitable for firing on ceramic compositions for dental purposes consisting essentially of 1–70 weight % palladium, 0.1–35 weight % chromium, also containing an element which is scandium, yttrium, lanthanum, another rare earth or mixture of such elements, such element or mixture of elements being present in an amount of up to 8 weight %, and containing aluminum, silicon, tin, indium, gallium, or mixture thereof, said aluminum, silicon, tin, indium, gallium, or mixture thereof being present in an amount of up to 5 weight %, and the balance consisting essentially of cobalt.

* * * * *